United States Patent [19]
Melendez et al.

[11] Patent Number: 5,464,773
[45] Date of Patent: Nov. 7, 1995

[54] CELL DISRUPTING APPARATUS

[75] Inventors: Luis A. Melendez, Norwood; Robert E. Rosenbaum, Framingham; Marcela A. Vera-Garcia, Framingham; D. Michael Olive, Framingham; John E. Swenson, Marlboro, all of Mass.

[73] Assignee: Amoco Corporation, Chicago, Ill.

[21] Appl. No.: 213,194

[22] Filed: Mar. 14, 1994

[51] Int. Cl.$^6$ .................................................. C12M 1/33
[52] U.S. Cl. .................. 435/306.1; 435/259; 435/283.1; 241/2; 241/175; 366/209
[58] Field of Search .......................... 435/29, 267, 270, 435/287, 288, 289, 291, 316, 803, 820, 259; 366/219, 237, 208, 209, 216; 241/2, 36, 175, 179

[56] References Cited

U.S. PATENT DOCUMENTS

| | | | |
|---|---|---|---|
| 3,286,739 | 11/1966 | Ikakura | 139/389 |
| 3,286,939 | 11/1966 | Karpenko et al. | 241/175 |
| 4,125,335 | 11/1978 | Blume et al. | 366/209 |
| 4,202,634 | 5/1980 | Kraft et al. | 366/208 |
| 4,295,613 | 10/1981 | Moore et al. | 241/2 |
| 4,829,230 | 5/1989 | Perry et al. | 494/88 |
| 4,874,137 | 10/1989 | Chiba | 241/2 |

OTHER PUBLICATIONS

Foster. "Cell Disruption: Breaking Up is Hard to Do". Biotechnology vol. 10 (1992) pp. 1539–1541.
F. O. Schmitt, C. H. Johnson and A. R. Olson. *Oxidation Promoted By Ultrasonic Radiation*. Chemical Laboratory of Univ. of Cal. Feb. 1929, vol. 51, pp. 370–375.
E. S. Maculla and P. B. Cowles. *The Use Of Glycine in the Disruption of Bacterial Cells*. Science, Apr. 9, 1948, vol. 107, pp. 376–377.
H. K. King and H. Alexander. *The Mechnical Destruction of Bacteria* Univ. of Edinburgh, 1948, pp. 315–324.
H. Mickle. *Il.–Tissue Disintegrator*. Journ. R. MICR. SOC., 1948, pp. 10–12.
P. M. Nossal, *A Mechanical Cell Disintegrator*. Biochemistry Dept., Univ. of Adelaide, Austral, 1953; 31. pp. 583–590.
R. Davies. *Observations On The Use Of Ultrasound Waves For The Disruption of Micro–Organisms*. Biochemistry Dept., Univ. of Cambridge, (Great Britain) Aug. 6, 1958, vol. 33, pp. 481–493.
P. Doty, B. Bunce McGill, and S. A. Rice. *The Properties Of Sonic Fragments Of Deoxyribose Nucleic*. Chemistry Dept. Harvard Univ. Cambridge, Mass., Mar. 25, 1958, vol. 44, pp. 432–438.
C. Lamanna and M. F. Mallette. *Use Of Glass Beads for The Mechanical Rupture Of Microorganisms In Concentrated Suspensions*. Microbiology and Biochemistry Dept., Johns Hopkins Univ. School of Hygiene and Public Health, Baltimore, Md., Nov. 16, 1953, pp. 503–504.
B. S. Roberson and J. H. Schwab. *Studies On Preparation Of Bacterial Cell Walls And Criteria Of Homogeneity*. Biochimica et Biophysica ACTA 44, Univ. of N.C School of Medicine, Apr. 12, 1960, pp. 436–444.
A. Rodgers and D. E. Hughes. *The Disintegration Of Micro–organisms By Shaking With Glass Beads*. Journ. of Biochemical and Microbiological Tech. and Eng. vol. II, No. 1. 1960, pp. 40–70.

(List continued on next page.)

*Primary Examiner*—William H. Beisner
*Attorney, Agent, or Firm*—Thomas Tolpin

[57] ABSTRACT

An improved apparatus for effectively disrupting biological samples contained in cuvettes to which beads have been added. In the apparatus, a special arm/bearing subassembly is driven and oscillated by a motor in a manner to attain cellular disruption of the biological samples without degradation of their cellular components. In the preferred form, the special arm/bearing subassembly has a cam, bearings, and a bearing sleeve which cooperate with a motor drive shaft to rotate a yoke with two arms holding four cuvettes. For increased safety and environmental protection, special sample retainers can be provided to better secure the cuvettes and the arm/bearing subassembly is enclosed in a sample chamber which provides a secondary containment compartment that contain any spillage.

8 Claims, 4 Drawing Sheets

OTHER PUBLICATIONS

W. R. Johnson and C. C. Rice. *Shear Degradation Of Vinly Polymers In Dilute Solution By High–Speed Stirring.* Journal of Polymer Science, vol. XIV, 1960, pp. 217–225.

D. E. Hughes. *The Disintegration Of Bacteria And Other Microorganisms By the M.S.E.–Mullard Ultrasonic Disintegrator.* Journal of Biochemical and Microbiological Tech. and Eng., vol. III, No. 4, 1961, pp. 405–433.

F. D. Rumscheidt and S. G. Mason. *Particle Motions In Sheared Suspensions.* Journal of Colloid Science 16, 1961, pp. 238–261.

P. B. Hamilton and S. G. Knight. *Ballistic Disruption of Penicillium Chrysogenum Cells.* Dept. of Bacteriology, Univ. Wis. Madison, Jun. 15, 1962, pp. 577–579.

D. E. Hughes and W. L. Nyborg. *Cell Disruption by Ultrasound.* Science vol. 138., Oct. 12, 1962, pp. 108–114.

S. A. Hawley, R. M. Macleod, and F. Dunn. *Degradation Of DNA By Intense, Noncavitating Ultrasound.* The Journal Of The Acoustical Society Of America, vol. 35, No. 8, Aug. 1963, pp. 1285–1287.

O. C. Richards and P. D. Boyer. *Chemical Mechnanism Of Sonic, Acid, Alkaline And Enzymic Degradation Of DNA.* J. Mol. Bio. (1965)II, pp. 327–340.

E. A. Neppiras and D. E. Hughes. *Some Experiments On The Disintegration of Yeast By High Intensity Ultrasound.* Biotechnology and Bioengineering, vol. VI., 1964, pp. 247–270.

J. W. T. Wimpenny Ph.D. *Breakage Of Micro–Organisms.* Process Biochemistry, Jul. 1967, pp. 41–44.

A. R. Peacocke and N. J. Prichard. *The Ultrasonic Degradation Of Biological Macromolecules Under Conditions Of Stable Cavitation. II. Degradation Of Deoxyribonucleic Acid.* Biopolymer, vol. 6, 1968, pp. 605–623.

J. Rehacek, K. Beran and V. Bicik. *Disintegration Of Microorganisms And Preparation Of Yeast Cell Walls In A New Type Of Disintegrator.* Applied Microbiology, Mar. 1969, pp. 462–466.

E. Work. *Cell Walls* Mehtods In Microbiology, vol. 5A, 1971, pp. 361–418.P.

D. E. Hughes, J. W. T. Wimpenny and D. Lloyd. *The Disintegration Of Micro–Organisms.* Norris, Ribbons 1971, Microbiology Department, Univ. College, Cardiff, Glam., pp. 1–53.

C. J. James, W. T. Coakley and D. E. Hughes, *Kinetics Of Protein Release From Yeast Sonicated In Batch And Flow Systems At 20kHz.* Biotechnology and Bioengineering, vol. XIV, 1972, pp. 33–42.

J. A. Rooney. *Shear As A Mechanism For Sonically Induced biological Effects.* The Journal Of the Acoustical Society Of America, vol. 52, No. 6 (Part 2) May 12, 1972, pp. 1718–1724.

J. A. Currie, P. Dunnill and M. D. Lilly. *Release Of Protein From Bakers' Yeast (Saccharomyces Cerevisiae) By Disruption In An Industrial Agitator Mill.* Biotechnology and Bioengineering, vol. XIV, (1972), pp. 725–736.

F. Marffy and M. R. Kula. *Enzyme Yields From Cells Of Brewer's Yeast Disrupted By Treatment In A Horizontal Disintegrator.* Biotechnology and Bioengineering, vol. XVI, (1974), pp. 623, 634.

A. Helenius and K. Simons. *Solubilization Of Membranes by Detergents.* Biochimica et Biophysica Acta, 415 (1975) pp. 29–79.

W. T. Coakley, A. J. Bater and D. Lloyd. *Disruption Of Micro–Organisms.* Adv. Microlo. Physiol. 16 (1977) pp. 279–341.

W. B. Clark, L. L. Bammann and R. J. Gibbons. *Comparative Estimates Of Bacterial Affinities And Adsorption Sites On Hydroxyapatite Surfaces.* American Society For Microbiology, vol. 19, No. 3, pp. 846–853 (1978).

R. W. H. Verwer, E. H. Beachey, W. Keck, A. M. Stoub and J. E. Poldermans. *Oriented Fragmentation Of Escherichia Coli Sacculi By Sonication.* Journal Of Bacteriology, Jan. 1980, pp. 327–332.

C. A. Schnaitman. *Cell Fractionation.* Gerhardt, p. ed., 1981, pp. 52–61.

A. S. Fischel and G. M. Carman. *Phosphatidylinositol Biosynthesis In Saccharomyces Cerevisiae: Purification and Properties of Microsome Associated Phosphatidylinositol Synthase.* Journal of Bacteriology, Apr. 1983, pp. 304–311.

D. A. Dooley, P. G. Sacks and Morton W. Miller. *Production Of Thymine Base Damage In Ultrasound–Exposed EMT6 Mouse Mammary Sarcoma Cells.* Radiation Research 97, 1984, pp. 71–86.

T. Kondo, S. Arai, M. Kuwabara, G. Yoshii and E. Kano. *Damage In DNA Irradiated With 1.2 MHz Ultrasound and Its Effects On Template Activity Of DNA For RNA Synthesis.* Radiation Research 104, 1985, pp. 284–292.

A. F. Kalb, J. C. Loper, C. R. Dey, C. W. Woods and T. R. Sutter. *Isolation Of A Cytochrome P–450 Structural Gene From Saccharomyces Cerevisiae.* Dept. of Microbiology and Molecular Genetics, and Department of Environmental Health, Univ. of Cincinnati College of Medicine, Cincinnati, Ohio, 1986, pp. 237–245.

M. R. Kula and H. Schutte. *Purification Of Proteins And The Disruption Of Microbial Cells.* Biotechnology Progress (vol. 3 No. 1) Mar., 1987, pp. 31–42.

H. Schutte and M. R. Kula. *Analytical Disruption Of Microorganisms In A Mixer Mill.* Enzyme Microb. Technol., 1988, vol. 10, pp. 552–558.

U. Bakir, H. A. Kocak, H. Hammamci. *The Construction And Use of Bead Mill For The Extraction Of Intracellular Proteins.* Doga Tu Biolo.(Genetics, Microbiology, Molecular Biology, Cytology) Mar. 12, 1988, pp. 170–175.

W. Hummel and M. R. Kula. *Simple Method For Small–Scale Disruption Of Bacteria And Yeasts.* Journal Of Microbiological Methods (9), 1989, pp. 201–209.

S. Raha, F. Merante, G. Proteau and J. K. Reed. *Simultaneous Isolation Of Total Cellular RNA and DNA From Tissue Culture Cells Using Phenol And Lithium Chloride.* GATA 7(7), 1990, pp. 173–177.

Pritchard et al. "The Ultrasonic Degradation of Biological Macromolecules Under Conditions of Stable Cavitation". Biopolymers. vol. 4(1986) pp. 259–273.

CELL DISRUPTING APPARATUS

This invention relates to biotechnology equipment and more particularly, to an apparatus which disrupts the cellular integrity of biological samples.

BACKGROUND OF THE INVENTION

The science of biotechnology is constantly improving investigators' capability to detect and analyze various intracellular components, such as DNA, RNA, membranes and organelles. However, in order for any assay to detect these intracellular components, the various probes or other assay reactants must be able to physically reach and interact with their targets. This may be a troublesome task when the sample is difficult to disrupt or lyse, and in these situations, the accuracy of the assay may be compromised.

A second instance where cellular disruption is important is the harvesting of products manufactured by a cell or tissue, whether the products be naturally occurring metabolites or the result of the introduction of a heterologous gene(s) into the organism's genetic apparatus.

If methods used to disrupt the cell are too harsh, the integrity of the intracellular components may be lost. The challenge for the researcher then is to liberate as many intracellular components as possible from the confines of the cell, but at the same time not destroy the cellular components. The difficulty in achieving a workable balance between cellular disruption and component preservation is summarized in Foster, 1992 "Cell Disruption: Breaking Up Is Hard to Do" *Bio/Technology* 10:1539–1541.

Some methods used in the past to disrupt cells have included chemical systems (such as the use of enzymes or other chemicals to destroy the integrity of cell wall and/or membrane), and mechanical systems, (such as ball mills or the application of high pressure using the so-called "French Press"). The use of enzymes is not preferred in most commercial applications because of cost and extended incubation times. In addition, the choice and amounts of appropriate enzyme(s) must be determined for each species cultured, and some cells (particularly certain bacteria and fungi) are particularly resistant to enzymatic attack. Mechanical systems such as the French Press, use high pressures to disrupt the cell system, but this usually results in the generation of heat, which may degrade the cellular components of interest. Another problem associated with the French Press is that it is not suitable for the handling of pathogenic organisms. Further, when processing multiple samples, there is a possibility for cross-contamination. Non-invasive sonication is another technique, but has not proven to be uniformly successful with all cell types, notably yeast.

At present the technique of choice is "bead-beating" where small glass or zirconium beadlets are added to the sample tube. Upon shaking, the beads collide in the sample to facilitate the disruption process. Examples of commercial cell disrupters include the BEAD-BEATER™ and MINI-BEADBEATER™ by Biospec Products (Bartlesville, Okla.) and the WIG-L-BUG by Cresent. The currently available bead-beating apparatae however, tend to overheat, and are restricted to processing a single sample. It would be most desirable to have an apparatus which combines the advantages of a prior art "bead-beating" apparatus without its disadvantages.

SUMMARY OF THE INVENTION

This invention is directed to a high precision reciprocating apparatus which is able to disrupt cellular integrity while not destroying cellular components. This is especially advantageous in the release of ribosomal targets for eventual RNA or DNA hybridization, or other analyses, and also in the release of cellular components for their harvesting. To accomplish this task, the apparatus moves one or more enclosed container(s) to which cellular material in need of disruption has been added along with cellular-disruption material. The movement of the container is of sufficient force so as to substantially sever cellular components of the cellular material for analysis or harvest in the absence of substantially damaging the cellular components.

The sample containers may be a vessel of virtually any type or material desired and appropriate for the given cellular material. Examples of preferred containers include cuvettes, test tubes, and glass or plastic vials.

The cellular-disruption material which is added to the sample container include those materials such as beads which are known in the prior art and are preferably made from zirconium oxide, but other materials such as ceramics, glass, metal, plastic or sand may also be used. In a preferred embodiment of the invention, a volume of approximately 400 µl of zirconium oxide beads of two sizes are used together, such as approximately 0.7 g of 0.1 mm diameter beads and 0.65 g of 0.5 mm diameter beads. Those of skill in the art will appreciate that other sizes, amounts, and combinations can be employed.

While devices utilizing small bead particles have been used in the past, the theoretical basis of how lysis is achieved has not been thoroughly investigated. Lysis appears to be the result of both physical destruction of the cellular integrity by collisional interaction with solid particles, and cavitation which leads to vibrations which rupture cells. It has been found in accordance with this invention, that slow speed stirring of samples in a non-cavitational regime resulted in a only a little lysis. Therefore, one aspect of this apparatus of the invention is to provide enhanced cavitation.

Virtually any type of biological sample may be disrupted using the apparatus of this invention. As used throughout the specification and claims, the term "cellular material" is intended to have its broadest possible meaning, and specifically includes: prokaryotic organisms including bacteria; eukaryotic cells and organisms such as fungi, plant cells and tissues, animal cells and tissues, and even protoplasts, spheroplasts and spores; and biological materials which are not technically "cells" but which are in need of disruption (such as viruses and the like). As the samples being processed are preferably in an enclosed chamber, the apparatus of this invention is well-suited for the processing of pathogenic organisms as well as non-pathogenic ones. This apparatus is also well suited for suspending particulate materials in a medium, which need not be liquid. The materials involved in this use of the apparatus need not be "biological" in nature, but may be any particulate material and virtually any medium.

One preferred embodiment of the apparatus of this invention is able to process a plurality of samples simultaneously. In the prior art, the apparatus could only accommodate a single sample at any given time. When multiple samples needed disruption, the time required for completing the entire batch was extended, and there was greater wear and tear on the motor. In contrast, with the apparatus of this invention, one can choose to process either a single sample or a plurality of samples. In one embodiment, a maximum of four samples can be processed at a given time. In yet another embodiment, a maximum of eight samples can be processed. Thus the apparatus of this invention allows for much greater processing efficiency than was heretofore possible, while at the same time preventing undue wear and tear on the motor.

Further, the sample container size may be adjusted, so a large variety of samples volumes may also be processed simultaneously.

It is preferred that the movement imparted to the containers be a vibrational movement, and in particular an oscillating movement. The sample container(s) is preferably carried on an arm/bearing subassembly, driven by an electric motor. The arm/bearing subassembly comprises the arm, a mechanism for affixing each container to the arm; a bearing which is in contact with the bearing sleeve, which in turn is in contact with the arm; an eccentrically angled cam which rides in the bearing; and a spring which converts the rotational movement supplied by the motor into movement described by the eccentrically angled cam, so that the arm oscillates at a displacement from the horizontal position of from about 4 to about 7 degrees.

It has been found in accordance with this invention, that the rate of oscillation affects the degree of cell lysis. Some prior art machines, shake samples at a rate of approximately 3,000 oscillations per minute. The aforementioned BEAD-BEATER™ device employs an oscillation rate of approximately 5,000 oscillations per minute. In accordance with this invention, it has been found that the optimum cell lysis with minimum destruction of released cellular components generally occurs at speeds of approximately 3,000–7,000 oscillations per minute, and thus the apparatus of the present invention provides an oscillation rate of approximately 3,000 to 7,000 oscillations per minute, preferably between 4,750 to 5,250 oscillations per minute, and more preferably approximately 5,000 oscillations per minute. It has been found that speeds greater than about 7,000 oscillations per minute can lead to sample container failure.

Unfortunately, in prior art machines there is a tendency for the motor to slow as it heats up. The inventive apparatus overcomes this problem, because the motor has a motor speed control means comprising an electronic speed sensor and speed wheel which generates electronic feedback to maintain constant motor speed regardless of operational temperature or fatigue. The result is increased reproducibility of the sample processing.

It has also been found in accordance with this invention that the angular displacement of the oscillating arm from the motor's vertical axis affects the efficiency of the cellular disruption operation. In accordance with this invention, it has been found that the magnitude of displacement is preferably approximately 4 to 7 degrees, and preferably about 5 degrees. It has been found that a lower angular displacement, such as approximately 3.5 degrees gives a decrease in cellular disruption efficiency, whereas displacements greater than 7 degrees results in degradation of the cellular component or product. Therefore, in a preferred embodiment, the arm/bearing subassembly maintains an angular displacement of between 4 and 7 degrees from the vertical axis, and preferably about 5 degrees.

A further feature of the disruption operation is the time of oscillation. It has been found in accordance with this invention that for a given speed and angular displacement, there is an optimum time of operation. Oscillation for times less than the optimum will result in less cellular disruption, and further oscillation will result in increased degradation of cellular components or products. Accordingly, one embodiment of the apparatus of this invention includes a fixed timer. While optimum parameters will vary with the sample being disrupted, it has been found that overall, a preferred apparatus will oscillate the sample at about 4,750–5,200 oscillations per minute, with an angular displacement of approximately 5 degrees for approximately 3–9 minutes, preferably for about 6 minutes. Thus, one preferred embodiment has a fixed timer to control length of processing, and this is set at six minutes. In another embodiment, the operator may adjust the setting of the timer.

A further aspect of this invention involves the addition of various surfactants and/or detergents to the liquid cell sample in order to enhance lysis. Additions of such surfactants and/or detergents also apparently changes the surface tension of the sample, and allows for more stable temperatures of the samples. In some samples, lysis in the absence of detergents can result in a temperature increase of up to 25° C., which can adversely impact the sample quality. Addition of surfactants and/or detergents has been observed to result in a temperature increase of only approximately 12° C. Preferred surfactants include saponin and preferred detergents include Sarkosyl (N-Laurylsarcosine), and CTAB (cetyltrimethyl ammonium bromide), although one of ordinary skill in the art will appreciate others may be satisfactorily substituted.

This invention also includes a method of disrupting cellular material which includes the steps of: substantially enclosing the cellular material and a cellular-disrupting material in a container; and shaking the container for a period of time greater than 3.5 minutes in the absence of substantially degrading the cellular components. This process further comprises the step of harvesting the liberated cellular components. Harvesting steps can include separating the desired cellular components from the unwanted cellular material using, e.g. a centrifuge or filter. Harvesting may also include concentration and/or purifying steps.

The disrupting process may also include an analysis step. In this step, the liberated cellular components can be subjected to any number of analytical reactions and may include such steps as contacting the component with a component-detecting compound such as a probe, label, or reactant. Depending on the nature of the analysis step, qualitative and/or quantitative data may be obtained. Various appropriate assays are well known and it is well within the skill of the ordinary artisan to choose an appropriate assay.

Virtually any type of biological sample may be disrupted using the process of this invention. As the samples being processed are preferably in an enclosed chamber, the method of this invention is well-suited for use with pathogenic organisms as well as non-pathogenic ones.

One preferred embodiment of the method of this invention is able to disrupt the cellular contents of a plurality of samples simultaneously. Prior art processes were limited to a single sample at any given time. When multiple samples needed disruption, the time required for completing the entire batch was extended, and there was greater wear and tear on the equipment as well as an overall loss of efficiency. In contrast, with the process of this invention, one can choose to simultaneously disrupt either a single sample or a plurality of samples in a single container or multiple containers. In one embodiment, a maximum of four samples can be processed at a given time. In yet another embodiment, a maximum of eight samples can be processed. Further, the sample container size may be adjusted, so a large variety of samples volumes may also be processed simultaneously.

It is preferred that the step of imparting movement to the containers be a step of imparting vibrational movement, and in particular an oscillating movement. The sample container(s) are preferably located on an arm/bearing subassembly, driven by an electric motor. The arm/bearing subassembly comprises the arm, a mechanism for affixing each container to the arm; a bearing which is in contact with the bearing sleeve which in turn is in contact with the arm; an eccentrically angled cam which rides on the bearing; and a spring which converts the rotational movement supplied by the motor into movement described by the eccentrically angled cam, so that the arm oscillates at a displacement from the horizontal position of from about 4 to about 7 degrees. Preferably, the process of the present invention includes providing an oscillation rate of approximately 3,000 to 7,000 oscillations per minute, preferably between 4,750 to 5,200 oscillations per minute, and more preferably approximately 5,000 oscillations per minute.

Another aspect of the process of this invention includes the step of regulating the motor speed. In a preferred process, the motor is controlled by a motor speed control mechanism comprising an electronic speed sensor and speed wheel which generates electronic feedback to maintain constant motor speed regardless of operational temperature or fatigue. Thus the process results in increased reproducibility of the sample disruption.

A further feature of the disruption process is the time of oscillation. Accordingly, one embodiment of the apparatus of this invention includes setting a fixed timer. While optimum parameters will vary with the cellular material being disrupted, it has been found that overall, a preferred process includes oscillating the sample at about 4,750–5,200 oscillations per minute, with an angular displacement of approximately 5 degrees for approximately 4–9 minutes, preferably for about 6 minutes.

A further aspect of this invention involves the step of adding various surfactants and/or detergents to the liquid cell sample in order to enhance lysis. Preferred surfactants include saponin, and preferred detergents to be added include Sarkosyl (N-Laurylsarcosine), and CTAB (cetyltrimethyl ammonium bromide). While the named surfactants and detergents are more preferred for best results, in some circumstances it may be desirable to use other surfactants or detergents.

A more detailed explanation of this invention is provided in the following description and appended claims taken in conjunction with the accompanying drawings.

DETAILED DESCRIPTION OF THE PREFERRED EMBODIMENT

Figure 1:
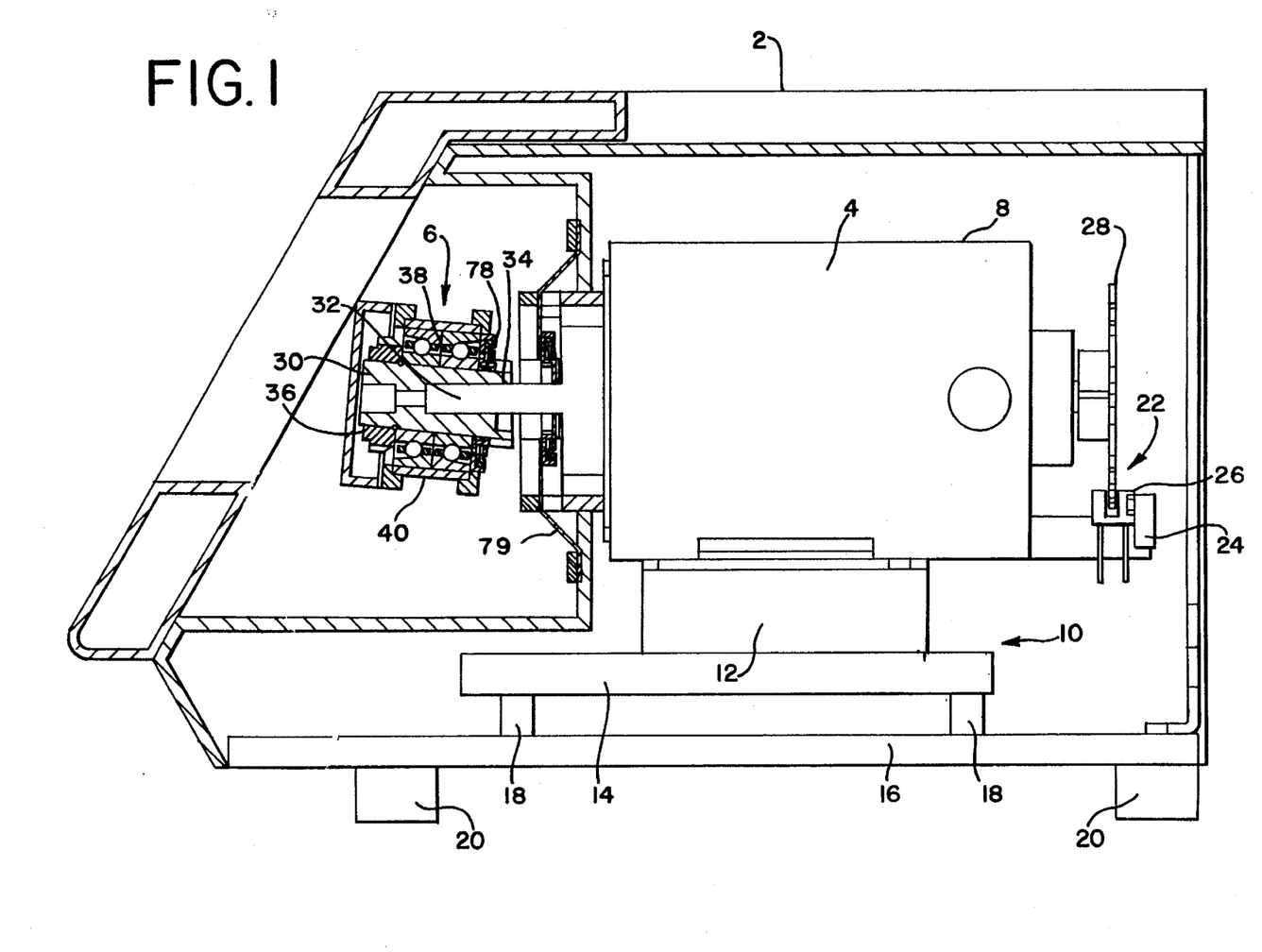
FIG. 1 shows a side cross-sectional view of the apparatus of this invention.

As shown in FIG. 1, an apparatus 2 provides a machine, device or instrument for disrupting cells. The apparatus 2 has a motor 4, preferably a heavy duty motor, such as at least ¼ horsepower, which is able to drive the bearing/arm subassembly 6 at an average of at least 5,000 oscillations per minute for periods of time up to approximately 9 minutes without generating excess heat. Surrounding the motor 4 is a motor housing 8. The motor housing 8 is a stressed member of the apparatus. To reduce vibrational movement and noise, the motor is preferably mounted on a motor drive subassembly 10. The motor drive subassembly 10 includes a pedestal providing a height spacer 12 welded, bolted or otherwise attached to a motor mount plate 14; both the motor and motor mount plate are allowed to vibrate. The vibrating motor mount plate 14 is connected to an elongated base plate 16 through a plurality of vibration dampening devices and isolators 18, such as elastomeric shims or feet creating a primary isolation stage. It was found that the addition of the vibrating motor mount plate resulted in a significant reduction in the operating noise of the machine. The apparatus has a set of leveling and isolation feet 20 which extend downwards from the base plate to create a secondary isolation stage.

Attached to the motor is a speed control mechanism 22. In the embodiment pictured, the speed control mechanism 22 is located at the rear of the motor, but it may be located elsewhere in other embodiments. The speed control mechanism 22 comprises an electronic speed sensor mount bracket 24, a speed sensor 26 which may be located on the rear of the speed sensor mount bracket, and a speed sensor wheel 28, which is mounted perpendicularly on the speed sensor. The speed control mechanism regulates the speed of the motor 4, as such motors have a tendency to increase or decrease speed after heat builds up. Thus the addition of the speed sensor 26 ensures more reproducible processing conditions. Preferably, the motor 4 also has a runoff protection mechanism which automatically shuts the motor off in the case of an uncontrolled increase or decrease in speed. This runoff protection means may preferably include a microprocessor.

Figure 6:
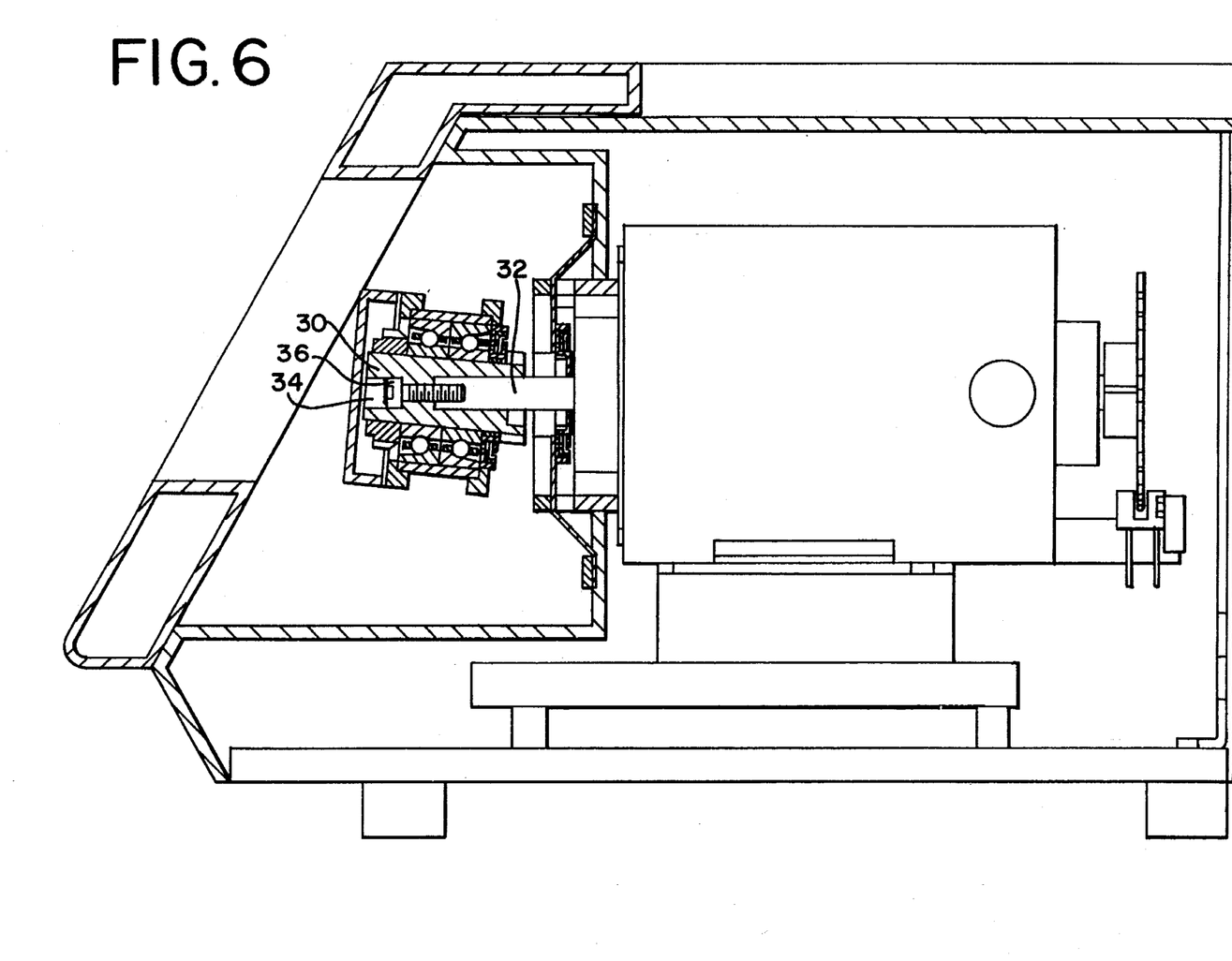
FIG. 6 shows a side cross-sectional view of the apparatus.

An elongated eccentrically angled cam 30 is driven by the motor shaft 32. The cam has a curved circular outer surface. Bearings 38 are pressed on to the curved outer surface of the cam. A shaft-receiving opening 34 extends longitudinally and eccentrically at an angle of inclination through the cam to securely engage and receive the motor shaft 32. The cam is securely held on the shaft by screw 36, as shown in FIG. 6.

Figure 2:
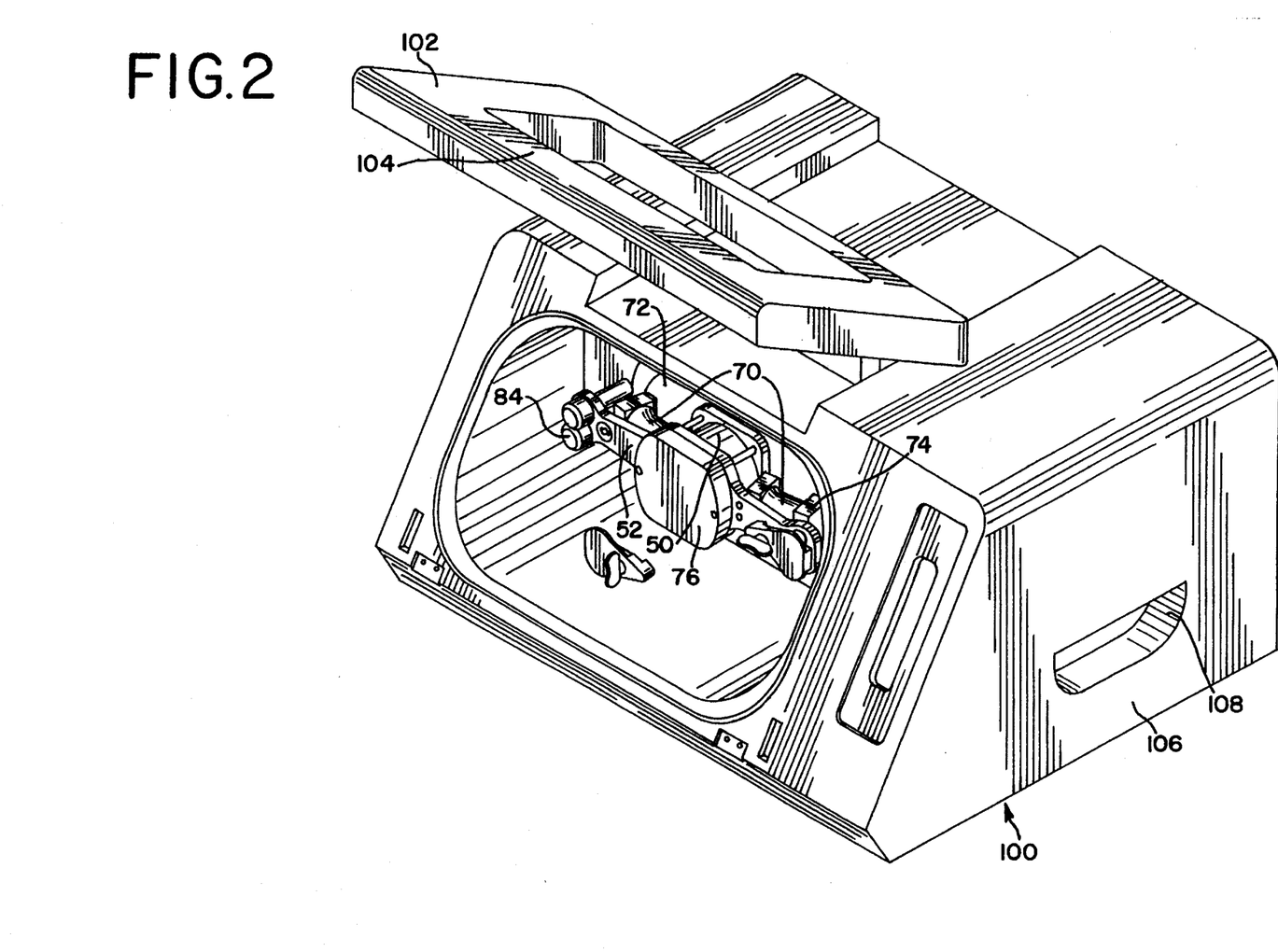
FIG. 2 is a perspective view of the front of the apparatus when the enclosure door is open, allowing access to the sample chamber.
Figure 4:
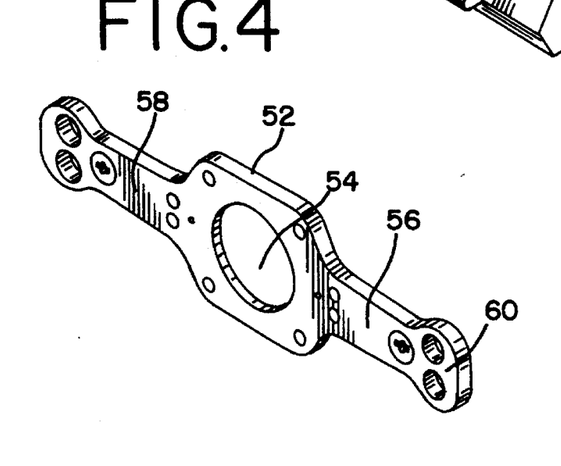
FIG. 4 is a perspective view of the yoke.
Figure 5:
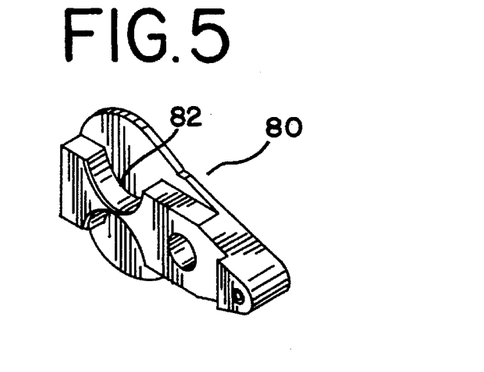
FIG. 5 is a perspective view of a sample retainer.

The motor drives the arm/bearing subassembly 6 which includes a set of angular contact bearings 38, held together by a bearing sleeve 40, mounted on the outer surface 50 of the eccentric cam 30. As shown in FIG. 4, an aluminum yoke 52 has an annular central portion 54 which rides upon and securely engages the bearing sleeve 40. The yoke 52 has a pair of diametrically opposed elongated rectangular arms 56 and 58 which extend integrally outwardly from the central portion of the yoke. The outer ends of the arms 56 and 58 comprise enlarged hand portions 60 with a convex curved outer edge and screw holes. A pair of teardrop-shaped gloves or sample retainers 80 shown in FIG. 5 can be fastened, such as by thumb screws or other fasteners, to the hands (ends) of the arms 60. The inner surface of each of the sample retainers has a pair of symmetrical concave, semicircular curved, arcuate flanges 82 which matingly engage and securely hold a pair of containers 84, such as cuvettes, tubes, or vessels to the arms to which it is associated (secured) as can be seen in FIG. 2. The arm and its attached cuvette(s) follow a path described by an eccentrically angled cam 30. An aluminum dust cap 76 and seal 78 prevent foreign matter from coming into contact with the arm/bearing subassembly.

Springs or dampening devices 70 prevent the arm from spinning directly with the motor, but allow the motion described by the shape of the cam, in this case an oscillation.

Figure 7:
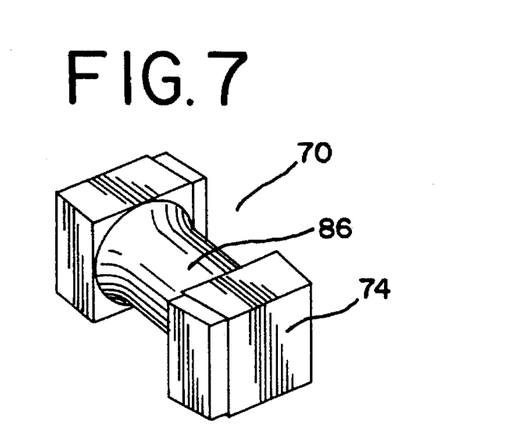
FIG. 7 is a perspective view of a dampening device.

The springs extend between and are attached to the arms 56, 58 and motor face plate 72. The springs (dampening devices) comprise a cylindrical elastomeric rubber body 86 between rubber coated metal plates 74. The springs are preferably made from a resilient material such as natural rubber, or a rubber-like plastic. It has been found that many types of metal springs function for only a short time before they fail.

A protective seal 78 and a flexible seal 79 define a sample chamber area, providing an interior compartment, which separates the arm and bearing subassemblies from the remainder of the motor 4. The advantages to this design and arrangement are twofold: if a sample cuvette should break, cleanup of any spillage is easily accomplished. Secondly, any hazardous material which may spill out of the cuvette is confined to a single area. It is advantageous for the chamber area to be constructed with rounded corners so that cleanups can be easily accomplished. The shape and arrangement of the chamber provides a two-stage containment in case there is spillage when processing pathogenic material.

Figure 3:
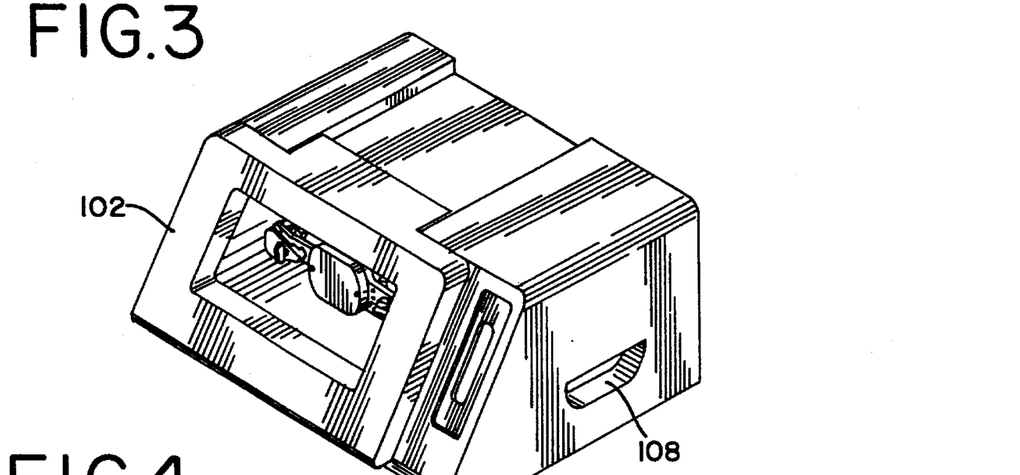
FIG. 3 is a perspective view of the front of the apparatus of FIG. 2, but with the enclosure door closed for disrupting cells.

The entire apparatus is enclosed in a housing 100, providing an enclosure with a front opening door 102. The door 102 is latched and/or hinged and may have a window 104. In one embodiment, the door 102 is made from a transparent or translucent plastic impact-resistant plastic such as acrylic resin. The door 102 protects against the possibility of aerosols being discharged should a sample cuvette leak or break, and it protects the operator against possible injury in the case of instrument malfunction. The sides of the housing 106 may have grip handles 108 to facilitate carrying and movement of the entire machine by the operator.

The apparatus of this invention is easy to maintain. Occasionally, the bearings 38 may require re-packing or replacement. Springs and seals which may need occasional replacement are located for easy accessibility.

Among the many advantages of the novel apparatus and process of this invention are:

Durability. The motor is a heavy-duty motor which will not burn out quickly as those of the prior art. Further, the ability to process a plurality of samples simultaneously results is less use of the motor, thus prolonging its life.

Reproducibility. The extent of the disruption is substantially equivalent for samples which are processed serially. This is accomplished by use of the speed controlling device to keep motor speed constant even when the motor heats up. In prior art, the motor would tend to slow when heated, resulting in less efficient disruption with later samples, which would adversely affect analyses run on the later samples.

Efficiency. One can process multiple samples with this machine simultaneously. In the prior art, only one sample could be processed at a given time.

Effective disruption without degradation. Various time/oscillation rate/angle of displacement parameters were found to influence the degree of cellular disruption and the quality of the liberated cellular components. These were optimized at 6 minutes, 5,000 oscillations per minute, and 5 degrees displacement. A second feature is the addition of a detergent or surfactant which helps preserve the integrity of the sample.

Safety. The chamber allows pathogens to be processed. Any aerosols or other potentially harmful substances are kept in the chamber. Also, should there be a malfunction of the motor, the loose parts would be enclosed, presenting minimal risk to the operator.

Although an embodiment of this invention has been shown and described, it is to be understood that various modifications and substitutions as well as rearrangement of parts, improvements, and process steps can be made by those skilled in the art without departing from the novel spirit and scope of the invention.

What is claimed is:

1. A cell disrupting apparatus, comprising:

container means for substantially enclosing cellular material and cell-disruption material, said container means comprising four containers; and container-moving means operatively connected to said container means for moving said container means with sufficient force to shake said cellular material in the presence of said cellular-disrupting material so as to substantially sever cellular components of said cellular material for analysis or harvesting in the absence of substantially damaging said cellular components; said container-moving means not comprising a curved strap restricting the shaking movement; and said container-moving means comprising:

a substantially horizontal shaft;

a motor for rotating said horizontal shaft;

an eccentric cam secured to said shaft; bearings mounted on said cam;

a bearing sleeve positioned about and mounted on said bearings;

a yoke having a central portion riding upon and secured to said bearing sleeve, said yoke having a pair of diametrically opposed elongated arms extending integrable outwardly from said central portion for holding said four containers, each of said arms having an enlarged hand portion providing an outer end opposite said central portion, said enlarged hand portion having a convex outer edge and defining a pair of holes for receiving two of said containers;

springs attached to said arms and motor for preventing said arms from spinning directly with the motor and for converting rotational movement of the motor into movement described by said cam; and sample retainers fastened to the hand portions of said yoke, each of said sample retainers comprising a generally teardrop-shaped glove with a pair of substantially symmetrical concave flanges for matingly engaging and securing said two of said containers to said arms of said yoke.

2. An apparatus according to claim 1 wherein:

said cellular material comprises a member selected from the group consisting of: prokaryotic cells; eukaryotic cells and organisms, plant cells and tissues, animal cells and tissues; protoplast; spheroplasts; spores; and viruses; and said cellular-disrupting material is selected from the group consisting of ceramic beads, glass beads, zirconium beads, metal beads, plastic beads, and sand.

3. An apparatus according to claim 1 including a motor drive subassembly, comprising:

a motor mount pad positioned below said motor;

a pedestal attached to said motor mount pad and extending upwardly to said motor;

an elongated base plate positioned below said pedestal;

dampening devices extending between and connecting said elongated base plate and said motor mount pad; and leveling feet extending downwardly from said elongated base plate.

4. An apparatus according to claim 1 wherein said container-moving means comprises cam means including a speed sensing mechanism for sensing the speed of said motor, said speed sensing mechanism including:

a bracket disposed rearwardly of said motor;

a speed sensor mounted on said bracket for sensing the speed of said motor; and an upright wheel positioned substantially perpendicular to said speed sensor at a location rearwardly of said motor, and said wheel being connected to and driven by said motor for being sensed by said speed sensor.

5. An apparatus according to claim 1 defining a sample chamber substantially surrounding and enclosing said yoke, sample retainers and said four containers, said sample chamber providing an interior containment compartment to contain any spillage or breakage of said containers.

6. An apparatus according to claim 1 wherein said arms of said yoke oscillate at an angle of inclination ranging from about 4 degrees to about 7 degrees relative to said horizontal shaft.

7. A cell disrupting apparatus for oscillating and disrupting cellular material, in four containers in the absence of a curved strap, said cell disrupting apparatus comprising a substantially horizontal shaft;

a motor for rotating said horizontal shaft;

an eccentric cam secured to said shaft; bearings mounted on said cam;

a bearing sleeve positioned about and mounted on said bearings;

a yoke having a central portion riding upon and secured to said bearing sleeve, said yoke having a pair of diametrically opposed elongated arms extending integrable outwardly from said central portion for holding said four containers, each of said arms having an enlarged hand portion providing an outer end opposite said central portion, said enlarged hand portion having a convex outer edge and defining a pair of holes for receiving two of said containers;

sample retainers fastened to the hand portions of said yoke, each of said sample retainers comprising a generally teardrop-shaped glove with pair of substantially symmetrical concave flanges for matingly engaging and securing said two of said containers to said arms of said yoke;

springs attached to said arms and motor for preventing said arms from spinning directly With the motor and for converting rotational movement of the motor into movement described by said cam;

a motor mount pad positioned below said motor;

a pedestal attached to said motor mount pad and extending upwardly to said motor;

an elongated base plate positioned below said pedestal;

dampening devices extending between and connecting said elongated base plate and said motor mount pad;

leveling feet extending downwardly from said elongated base plate;

a bracket disposed rearwardly of said motor;

a speed sensor mounted on said bracket for sensing the speed of said motor; and an upright wheel positioned substantially perpendicular to said speed sensor at a location rearwardly of said motor, and said wheel being connected to and driven by said motor for being sensed by said speed sensor.

8. An apparatus according to claim 7 defining a sample chamber substantially surrounding and enclosing said yoke, sample retainers and said four containers, said sample chamber providing an interior containment compartment to contain any spillage or breakage of said containers.

* * * * *